(12) United States Patent
Minuth

(10) Patent No.: US 6,187,053 B1
(45) Date of Patent: Feb. 13, 2001

(54) PROCESS FOR PRODUCING A NATURAL IMPLANT

(76) Inventor: Will Minuth, Starenstrasse 2, D-93077 Bad Abbach (DE)

( * ) Notice: Under 35 U.S.C. 154(b), the term of this patent shall be extended for 0 days.

(21) Appl. No.: 08/970,804

(22) Filed: Nov. 14, 1997

(30) Foreign Application Priority Data

Nov. 16, 1996 (DE) ............................................... 196 47 531
Nov. 26, 1996 (DE) ............................................... 196 48 876

(51) Int. Cl.[7] .............................. A61F 2/08; C12M 1/10; A61L 27/00
(52) U.S. Cl. ................... 623/901; 623/23.72; 623/23.76; 435/285
(58) Field of Search .................................. 623/11, 12, 13, 623/15, 1, 66, 901, 23.72, 23.63, 23.55, 23.58; 435/285, 284; 128/898

(56) References Cited

U.S. PATENT DOCUMENTS 5,316,945 * 5/1994 Minuth ................................. 435/285
5,842,477 * 12/1998 Naughton et al. ..................... 623/11

FOREIGN PATENT DOCUMENTS 0 739 631   4/1996 (EP).
WO 94/20151   9/1994 (WO).

* cited by examiner

Primary Examiner—David J. Isabella
Assistant Examiner—Choon P. Koh
(74) Attorney, Agent, or Firm—Hoffman, Wasson & Gitler

(57) ABSTRACT

In a process for producing a natural implant for tissue of a human or animal body, the body's own cells are multiplied and/or differentiated on a cell base using a culture medium to form the implant.

20 Claims, 3 Drawing Sheets

PROCESS FOR PRODUCING A NATURAL IMPLANT

BACKGROUND OF THE INVENTION

The invention relates to a process for producing a natural implant. In known tissue engineering (WO 94/20151), it is conventional to use a three-dimensional cell base or matrix to which the cells are applied and in which the cells can be placed. This matrix may consist of a biodegradable substance, for example a lactic acid derivative (lactate). The matrix, due to stiffness requirements, it made as a relatively thick fabric. The matrix is coated with cement on which adhesion of the cells is enabled, for example, with polylysine. The cells are applied to this coated surface and are multiplied and differentiated in a perfusion chamber so that special properties can be formed.

This known process can be used to produce pieces of natural cartilage and bone. However, the production of pieces of tissue with a surface of a certain shape, such as a concave or convex surface with a given gradient, is not possible with this known process.

It is also a disadvantage of the known process, that substances, which can damage the cells or tissue, are re released from the lactate matrix. This matrix is necessary for reasons of stability.

the object of the present invention is the provision of a process for which the production of a natural implant is possible. This process does not require a lactate or polylactate matrix and allows for the production of surface shape.

SUMMARY OF THE INVENTION

In the process as claimed in the invention, a thin, membrane-like cell base is used as a support for the cells and does not form a three-dimensional skeleton in which the cells can be placed. the cell base can be a pattern of a body-compatible or biodegradable film, or flat material from the body, for example periosteum or perichondrium. In the process as claimed in the invention, a fabric-like or tissue-like structure which forms a three-dimensional skeleton for the cells and in which the cells can nest, is not necessary as the cell base. To enable three-dimensional multiplication of the cells, the cells, applied to the cell base, are coated with a material which corresponds to the material which enables healing of wounds in a human or animal body. For example, natural blood coagulate and/or a material which corresponds to natural blood coagulate and/or a fibrin cement and/or a collagen is suitable as this contact material. It is also possible to mix, or polymerize, the cells before application to the cell base with the material used for the coating and to then apply this mixture to the cell bases.

The coating then forms a skeleton in which the cells can multiply or spread three-dimensionally.

A thin cell base which does not exhibit mechanical stiffness or strength lies on the surface of a porous carrier. This surface is then shaped according to the surface desired for the implant, for example, concavely or convexly. The shape for the indicated surface can be determined diagnostically such that the indicated surface of the implant corresponds to the shape of the tissue in the area in which the implant is to be implanted.

With the process as claimed in the invention, natural implants for the most diverse tissues of the human or animal body, and also with the most varied functions, can be produced.

In the process as claimed in the invention, an exact surface shape for the produced implant can be achieved by shaping the porous carrier and the film-like cell base applied to this porous carrier. The shaping of the porous carrier can be done very exactly by removing and transferring the shape of a defective tissue region (for example, defective joint surface) with suitable technical aids in the required manner.

By means of the film-like cell base of the present invention, this surface shape is impressed on the cell formation which forms when the cells multiply, i.e. by means of the film-like cell base, the space for the three-dimensional multiplication of the cells is limited. A three-dimensional cell carrier is not needed in the invention, rather the material which promotes or enables healing in natural tissue offers the possibility of three-dimensional spreading or multiplication of cells.

The implant produced with the invention, on one side, has a boundary layer with a specific shape. Opposite this boundary layer, a cell structure is obtained which after implantation enables the implant to make contact with the existing natural tissue. By the coating of the cells applied to the cell bases, or by mixing these cells with the material which promotes or enables natural healing, the cells are caused during reproduction to form mortising surfaces on the implant side opposite the cell base, i.e. the aforementioned cell structures, with the possibility of making especially intensive contact with existing tissue so that after implantation rapid and uncomplicated growth of the implant into the natural tissue is ensured.

BRIEF DESCRIPTION OF THE DRAWINGS

The invention is detailed below by the following figures, which are illustrative of an embodiment of the invention.

DETAILED DESCRIPTION OF THE PREFERRED EMBODIMENT

The invention is detailed below using the figures, on one representative process, which is used to produce natural bone implant 4. In the figures, 1 is a hip joint. In the area of the joint surface 2, is a defect 3, which is to be corrected by natural implant 4, i.e. produced by an implant 4 from the patient's own cells.

Figure 1:
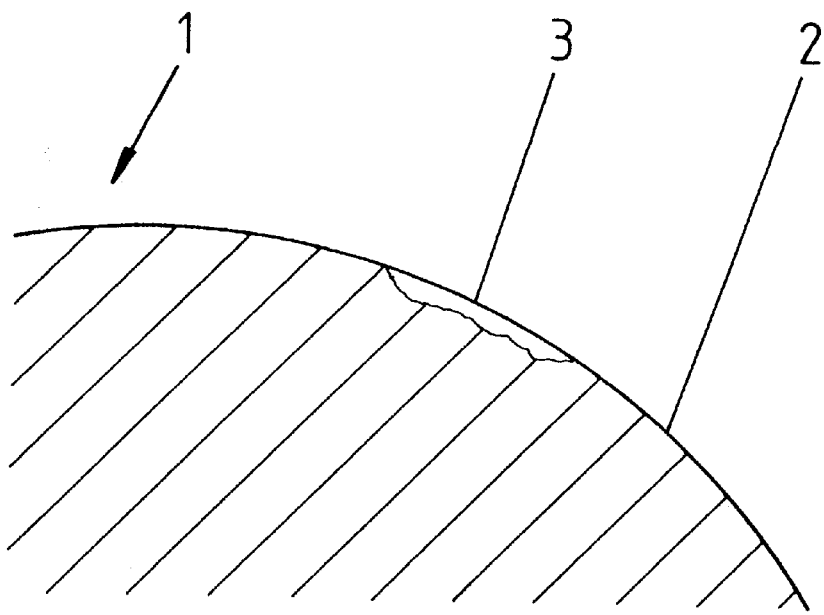
FIG. 1 shows, in a very simplified representation, a human joint, for example hip joint, with a defect on one joint surface.
Figure 2:
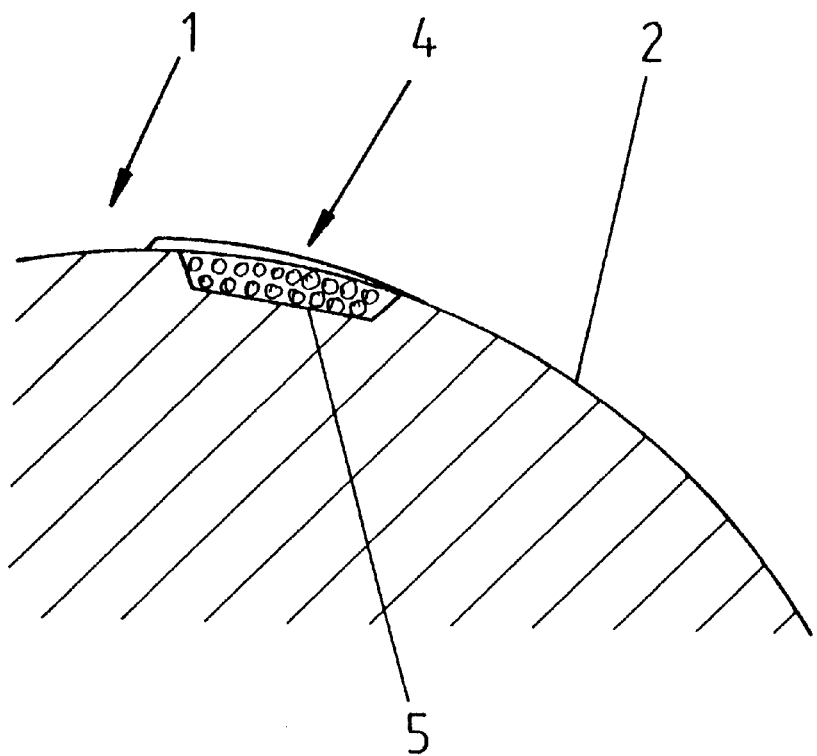
FIG. 2 shows the joint from FIG. 1 together with a natural implant used on the defective joint surface.
Figure 3:
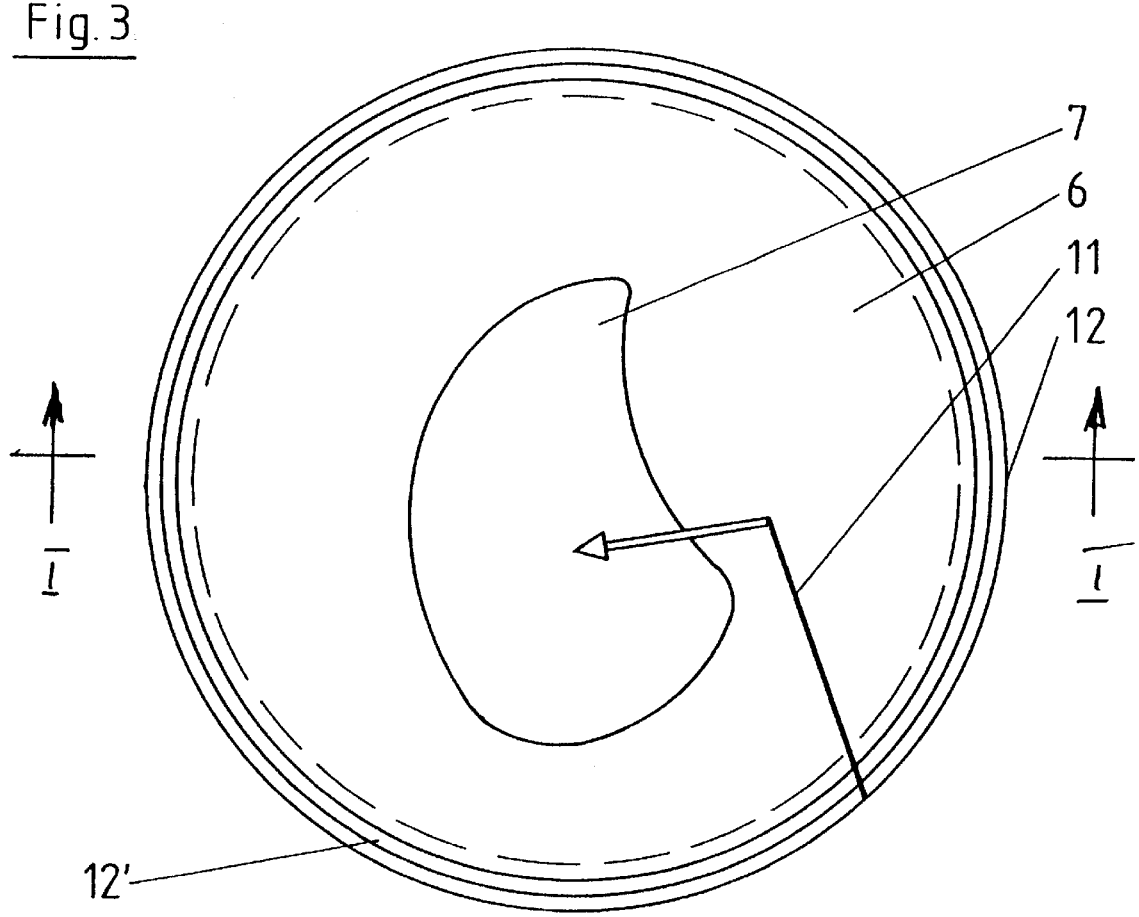
FIG. 3 shows a tissue carrier formed by a metal screen for producing the natural implant, together with a depression molded in this tissue carrier.
Figure 4:
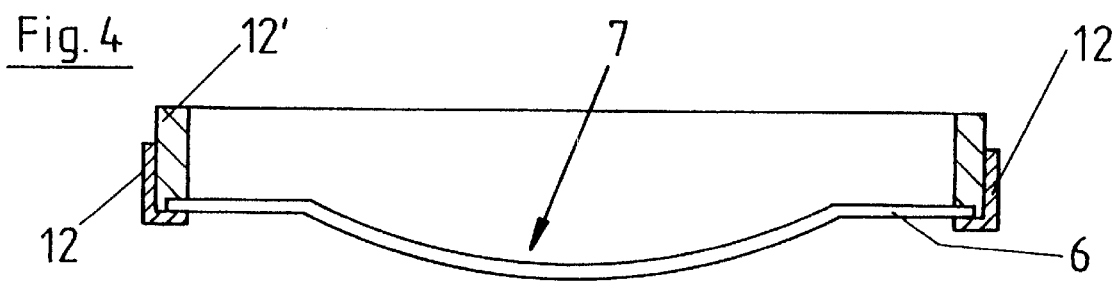
FIG. 4 shows a section corresponding to line I—I of FIG. 3.
Figure 5:
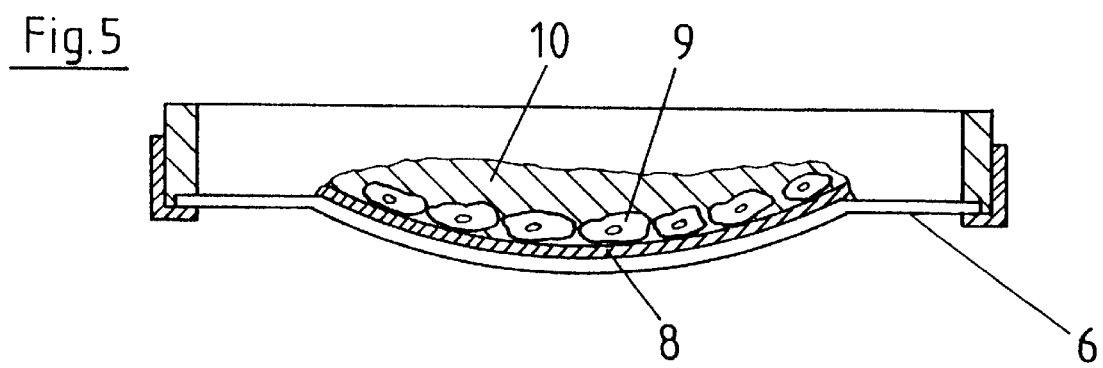
FIG. 5 shows a representation like FIG. 4, but with a thin cell carrier material inserted into the depression or cell base and with the patient's own cells growing on this cell base.

To produce implant 4, a disc-shaped porous carrier 6 (FIG. 3) is used. The porous carrier 6 can be made from a net-like or screen-like material of metal or plastic with sufficient strength. Depression 7 is shaped in carrier 6 and in its camber corresponds to the camber which joint surface 2 exhibited in the region of defect 3 and with a peripheral line which corresponds to the shape of implant 4 or recess 5 which accommodates this implant 4 in joint 2. The shape of depression 7 is determined with a suitable diagnostic process, for example, by means of computer tomography.

In depression 7, as the cell base material or cell support, a very thin membrane 8 is placed which is made from a material suitable as the base for the cells, for example, the patient's own natural pellicle. Membrane 8 can be made of plastic such as a Teflon which is suitable as the cell base. If desired, a membrane 8 is provided on the side away from carrier 6, with a cement which promotes adhesion of natural cells 9, such as a fibrin cement, collagen, natural blood coagulate, etc. Membrane 8 can be made of a natural skin, for example, periosteum or perichondrium, etc.

On the membrane or cell base 8, the patient's own cells 9 (cells which form cartilage or bone) are applied. The cell layer is then formed by cells 9, which is coated with a substance which promotes or enables natural growth or natural healing. As in natural wound healing, cells 9 can then spread three-dimensionally in this coating or layer 10. The coating 10 may be made from one of the following materials: fibrin cement, blood coagulate, extracellular matrix proteins. In addition, the coating 10 may contain one or more of these materials.

The material which forms coating 10 can be a fibrin cement and/or blood coagulate in mixture with an extracellular matrix protein.

Extracellular matrix proteins include collagen, materials such as collagen type II and/or type VI, chondronectin, fibronectin, vitronectin, proteoglycans, or glycoasmine glycans, such as, chondroitin sulfate, keratan sulfate.

Biodegradable fabric polymers, for example, polylactides, polyglycolic acids and/or polybutyric acids, can be added to the material which forms the coating.

Using retaining arms or retaining fingers 11, membrane 8, cells 9 and also coating 10 are kept on carrier 6. Spinning foot-like retaining fingers 11 can be attached to the carrier 6 or to a ring 12 which surrounds and bears this carrier 6. A clamping ring with which carrier 6 is attached in ring 12 is labeled 12'.

Figure 6:
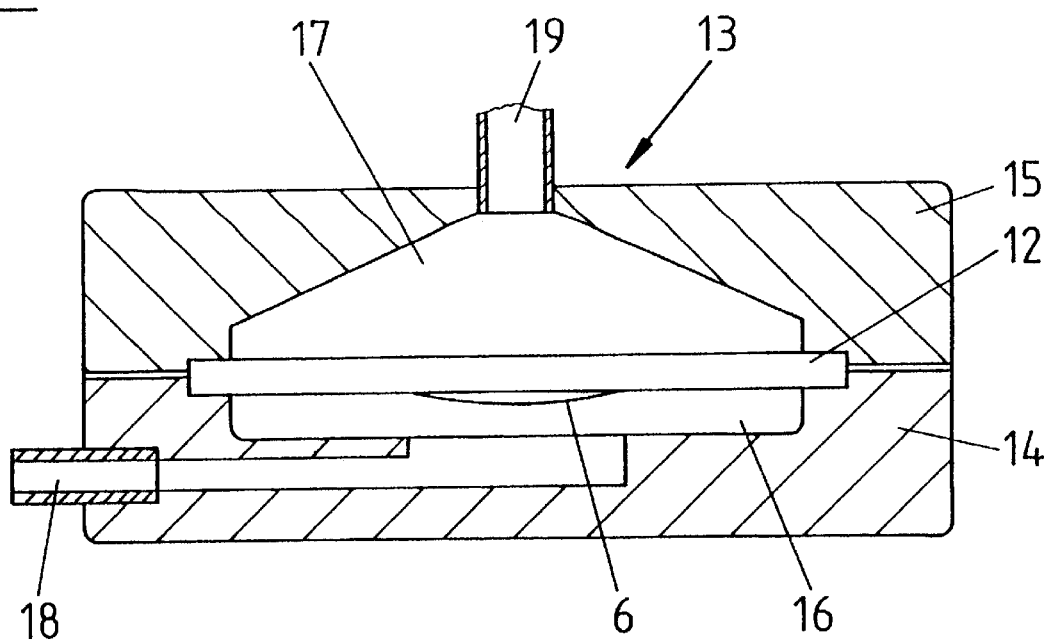
FIG. 6 shows, in a simplified representation and in a section, a perfusion chamber for supply of the patient's own cells during the formation of the natural implant.

Carrier 6 is inserted with membrane 8, cells 9 and coating 10 into a perfusion chamber 13, which is shown in FIG. 6, in cross section. Perfusion chamber 13 is made of two housing parts 14 and 15, of which housing part 14 forms lower chamber 16 and housing part 15 forms upper chamber 17. Between these two chambers, carrier 6 with membrane 8, cells 9, and coating 10 is arranged such that carrier 6 is in a horizontal or essentially horizontal plane and is facing lower chamber 16, while coating 10 is facing upper chamber 17. On lower chamber 16 is an inlet 18 for a liquid culture medium for supply of cells 9. On upper chamber 17 is an outlet 19 for draining the liquid culture medium which also contains metabolic products.

In the embodiment shown, the inlet and outlet are each located on the middle, over or under carrier 6, the culture medium flowing through and around chambers 16 and 17 each from bottom to top. The horizontal arrangement of carrier 6 ensures that disruptive components or metabolic products are removed optimally and quickly from cells 9.

After multiplication and differentiation of cells 9 in the perfusion chamber 13, the three-dimensional cell formation is removed from the opened perfusion chamber and from carrier 6 and inserted as an implant into recess 5 which is made in the joint during surgery. Coating 10 is then inside the joint in direct contact with the cartilage-bone boundary. Membrane 8 is on the outside and can be withdrawn after insertion of implant 4. It is also possible to leave membrane 8 on implant 4, especially when the membrane 8 is made of a body-compatible material which accumulates in the body. Membrane 8 is on the outside and is used, among other things, as a protective layer in the handling of the implant 4.

Produced implant 4 has the advantage that it consists solely of the patient's own cells. Because coating 10 lies on the inside on the cartilage-bone boundary, rapid healing or ingrowth of the implant 4 is ensured. The cell bases which had been conventional in the past in tissue engineering and which lead to high partial over acidification and the resulting tissue damage are avoided. Furthermore, it is possible, with the described process, to optimally match the shape of implant 4 to the respective natural shape of the tissue to be provided with the implant.

Figure 7:
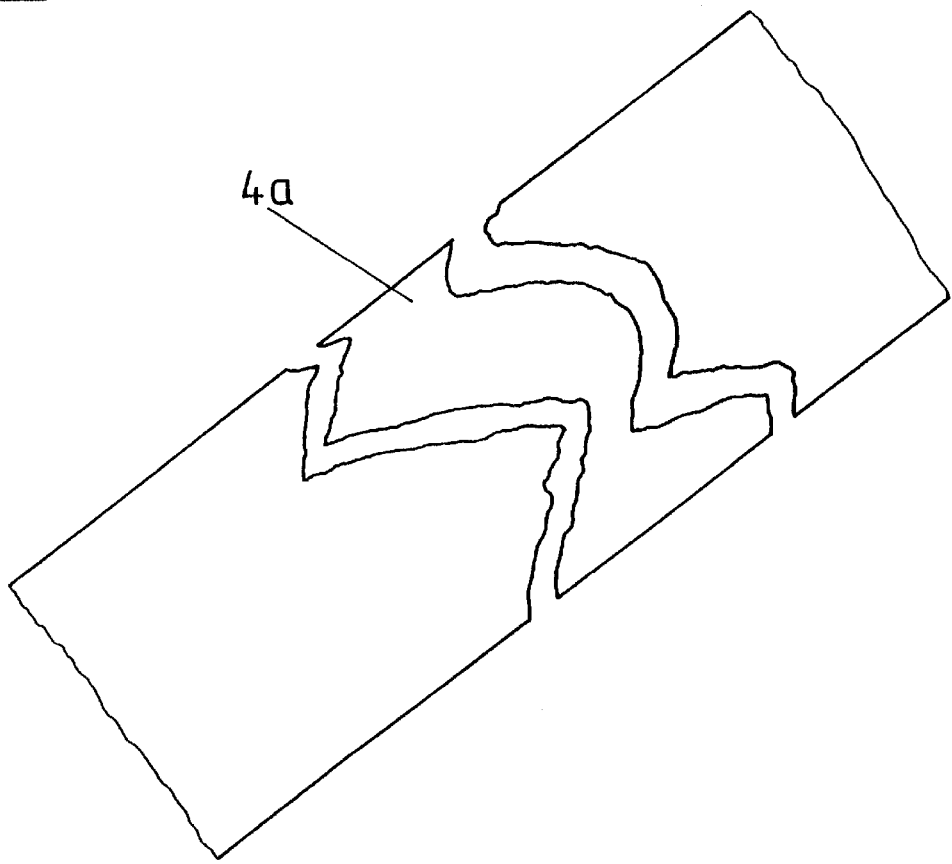
FIG. 7 shows, in a very simplified schematic, a splintered bone fracture with an implant which forms a growth bridge.

FIG. 7 shows in a very simplified representation a splintered bone fracture. An implant is labeled 4a which is inserted into this splintered bone fracture and which forms a type of growth bridge. Implant 4a is produced in the same manner as was described above for implant 4. A piece of periosteum, a material which enables tissue regeneration during natural bone healing, is suitable as membrane 8 or the cell base. Furthermore, the described process can also be used for implants for other tissue of the human or animal body. In particular, with the process as claimed in the invention, it is also possible to produce natural implants which are inserted as a module into certain tissues and which there assume functions of this tissue, for example the production of insulin, which (functions) are lost to the tissue for example by disease, etc.

The invention was described above using embodiments. It goes without saying that numerous alterations and modifications are possible without departing from the inventive idea on which the invention is based. Thus it is therefore also especially possible to change cells 9 before application to membrane 8 by genetic engineering, for example with a special growth gene in order to achieve accelerated growth and differentiation of cells 9 by the mitogenic and morphogenic substances produced by it.

What is claimed is:

1. A process for producing a natural implant for a human or animal body, wherein a body's own cells are multiplied or differentiated on a thin, film-like base using a culture medium to form said implant, said process comprising the steps of:

a) shaping a porous carrier in at least one surface region according to an external shape of a tissue into which said implant is to be implanted;
   b) placing said film-like cell base on said porous carrier;
   c) applying said body's own cells to said thin, film-like cell base;
   d) covering said thin film-like cell base with a coating material which causes or promotes natural healing, wherein said coating forming a skeleton into which said body's own cells can multiply and spread three-dimensionally to produce said natural implant; and
   e) multiplying said cells for forming said implant outside said human or animal body in a perfusion chamber, so that during growing of the implant, said liquid culture medium circulates alone all sides of the implant with said material which causes natural healing selected from the group consisting of fibrin, blood coagulate, extracellular matrix proteins, and combinations thereof.

2. The process as claimed in claim 1, wherein before application to said thin, film-like cell base, said body's own cells are mixed with a material which promotes or enables natural healing.

3. The process as claimed in claim 1, wherein said porous carrier is a screen-like or net-like material.

4. The process as claimed in claim 3, wherein said screen-like or net-like material is metal or plastic.

5. The process as claimed in claim 1, wherein said thin, film-like cell base is periosteum or perichondrium.

6. The process as claimed in claim 1, wherein said body's own cells are treated with a culture medium in a perfusion chamber in which said thin, film-like cell base is located substantially horizontally.

7. The process as claimed in claim 1, wherein said thin, film-like cell base and said body's own cells provided thereon are fixed by a mechanical means on said porous carrier.

8. The process as claimed in claim 1, wherein said thin, film-like cell base is provided with a medium which causes adhesion of said body's own cells before said body's own cells are applied.

9. The process as claimed in claim 1, wherein said thin, film-like cell base is provided with a fibrin cement before said body's own cells are applied.

10. The process as claimed in claim 1, wherein said extracellular matrix protein is a collagen material.

11. The process as claimed in claim 10, wherein said collagen material is collagen type II, collagen type VI, chondronectin, fibronectin, vitronectin, proteoglycans, or glycoasmine glycans.

12. The process as claimed in claim 11, wherein said glycoasmin glycans are selected from the group consisting of chondroitin sulfate and keratan sulfate.

13. The process as claimed in claim 1, wherein said coating material further comprises a biodegradable fabric polymer, selected from the group consisting of polyactides, polyglycolic acids and polybutyric acids.

14. A process for producing a natural implant for a human or animal body, wherein a body's own cells are multiplied or differentiated on a thin, film-like cell base using a culture medium to form said implant, said process comprising the steps of:

a) shaping a porous carrier in at least one surface region according to an external shape of a tissue into which said implant is to be implanted;

b) placing said film-like base on said porous carrier;

c) applying said body's own cells to said thin, film-like cell base which is mixed with a material which causes or promotes natural healing and forms a skeleton into which said body's own cells can multiply and spread three-dimensionally to produce said natural implant; and d) multiplying the cells for forming said implant outside said human or animal body in a perfusion chamber so that during growing of the implant, said liquid culture medium circulates along all sides of the implant, with said material which causes natural healing selected from the group consisting of fibrin, blood coagulate, extracellular matrix proteins and combinations thereof.

15. The process as claimed in claim 14, wherein before application to said thin, film-like cell base, said body's own cells are mixed with a material which promotes or enables natural healing.

16. The process as claimed in claim 14, wherein said porous carrier is a screen-like or net-like material.

17. The process as claimed in claim 16, wherein said screen-like or net-like material is metal or plastic.

18. The process as claimed in claim 14, wherein said thin, film-like cell base is periosteum or perichondrium.

19. The process as claimed in claim 14, wherein said body's own cells are treated with a culture medium in a perfusion chamber in which said thin, film-like cell base is located substantially horizontally.

20. The process as claimed in claim 14, wherein said thin, film-like cell base and said body's own cells provided thereon are fixed by a mechanical means on said porous carrier.

* * * * *